(12) United States Patent
Steinmeyer et al.

(10) Patent No.: US 8,509,873 B2
(45) Date of Patent: Aug. 13, 2013

(54) METHOD, TRANSDUCER, AND ARRANGEMENT FOR HIFU TREATMENT WITH MR TEMPERATURE MONITORING

(75) Inventors: Florian Steinmeyer, Herzogenaurach (DE); Michael Zwanger, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1202 days.

(21) Appl. No.: 12/030,257

(22) Filed: Feb. 13, 2008

(65) Prior Publication Data
US 2008/0194941 A1    Aug. 14, 2008

(30) Foreign Application Priority Data
Feb. 13, 2007   (DE) .......................... 10 2007 007 099

(51) Int. Cl.
*A61B 6/00*    (2006.01)
(52) U.S. Cl.
USPC ................................ 600/407; 600/411; 601/3

(58) Field of Classification Search
USPC ...................... 600/411, 407; 601/3
See application file for complete search history.

(56) References Cited

U.S. PATENT DOCUMENTS
5,443,068 A    8/1995  Cline et al.

FOREIGN PATENT DOCUMENTS
DE    2004 042 314 A1    3/2006

OTHER PUBLICATIONS
"Sample-Specific Diamagnetic and Paramagnetic Passive Shimming," Koch et al., Journal of Magnetic Resonance, vol. 182 (2008), pp. 68-74.

*Primary Examiner* — Long V. Le
*Assistant Examiner* — Nicholas Evoy
(74) *Attorney, Agent, or Firm* — Schiff Hardin LLP

(57) ABSTRACT

In a medical device with at least one transducer fashioned for generation of high-intensity focused ultrasound and with a magnetic resonance apparatus as well as associated ultrasound transducer, and method for generation of magnetic resonance exposures, at least one shim element is associated with the transducer for compensation of a susceptibility difference caused by the design of the transducer with regard to the transducer environment.

16 Claims, 3 Drawing Sheets

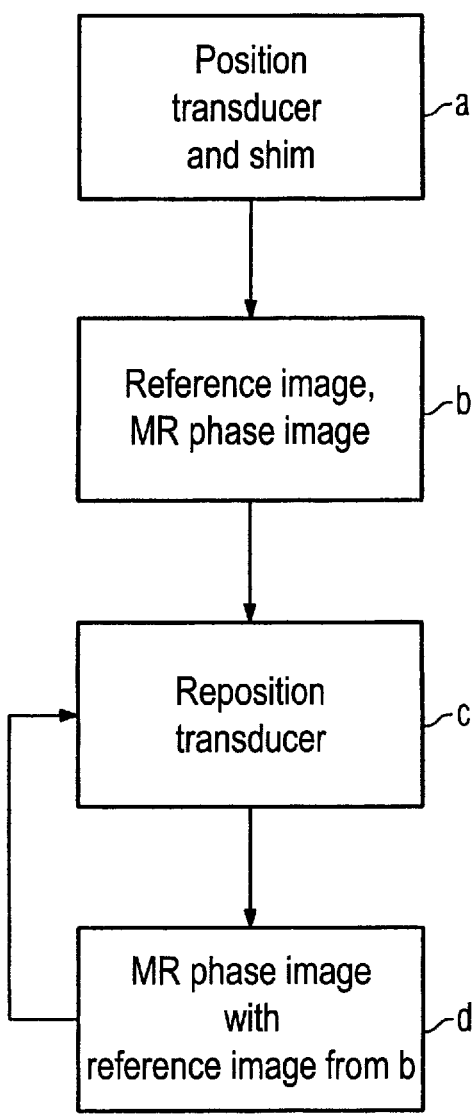

US 8,509,873 B2

METHOD, TRANSDUCER, AND ARRANGEMENT FOR HIFU TREATMENT WITH MR TEMPERATURE MONITORING

BACKGROUND OF THE INVENTION

1. Field of the Invention

The invention concerns a medical device having at least one transducer fashioned for generation of high-intensity focused ultrasound (HIFU), and with a magnetic resonance (MR) apparatus for generation of magnetic resonance exposures for a temperature monitoring as well as a corresponding transducer and a method for generation of magnetic resonance exposures for temperature monitoring of a region irradiated with high-intensity focused ultrasound.

2. Description of the Prior Art

High-intensity focused ultrasound (HIFU) is used in medicine, for example for tumor treatment. It is important to implement an accompanying temperature observation or monitoring in order to know whether the generated temperature is sufficient in order to destroy the tumor tissue and in order to ensure that the surrounding tissue is not affected by temperatures that are too high that may possibly cause permanent damage.

Conventionally, a temperature monitoring with the use of magnetic resonance phase images is implemented for such temperature monitoring. The temperature monitoring by magnetic resonance tomography is based on, for example, the proton resonance frequency shift that occurs when hydrogen bonds in water are attenuated due to thermal energy. It is problematic that this effect is relatively weak, such that phase difference images must be produced before and after the heating of the tissue. These images are subsequently subtracted to correct the effect.

Due to susceptibility changes that result, for example, in the environment of the image exposure region because the transducer for the generation of the high-intensity focused ultrasound used for treatment is filled with air, errors in the temperature measurement are caused when the transducer has moved in the time between acquisition of a reference image and a "temperature image".

It has been typical to either re-acquire a reference image for each new position of the transducer for generation of the ultrasound (which transducer is moved through a water bath arranged below the patient) in order to allow for the new susceptibility conditions, or to use an array of a number of transducers with which the focus can be varied without a position change of the array.

The acquisition of new reference images for each transducer position is comparably time-consuming and extends the duration of treatment of the patient. Moreover, the transducer arrays require a significant structural expenditure and have considerable manufacturing costs associated therewith.

SUMMARY OF THE INVENTION

An object of the present invention is to provide a medical device with at least one transducer fashioned for generation of high-intensity focused ultrasound and with a magnetic resonance apparatus for generation of magnetic resonance exposures for attendant temperature monitoring, wherein the medical device is improved with regard to the above items that in particular enables a reliable temperature monitoring.

In a device of the type described above, this object is achieved in accordance with the invention at least one shim element being associated with the transducer for compensation of a susceptibility difference that may exist relative to the transducer environment, the susceptibility difference being caused by the design of the transducer.

Magnetic susceptibility indicates the capability of a material to be magnetized in an external magnetic field, such as must be present for the acquisition of magnetic resonance images. The transducer that serves for generation of the ultrasound used for treatment (for example of a tumor) differs from its surroundings due to the material of which it is composed, in particular with regard to the fact that transducers normally embody materials of low susceptibility (for example, mostly ceramic piezo-material and an air-filled plastic housing). By contrast, the environment in which the transducer is located is normally a water bath or a gel mass or the like that serves for coupling the ultrasound with a treatment region or with a region to be irradiated for research purposes, such as a phantom or the like.

Accordingly, an embodiment of the transducer causes susceptibility changes or artifacts with regard to its environment, or with regard to the state that would exist if no transducer were present. According to the invention a shim element is therefore associated with the transducer.

The use of shim elements is known, for example from "Sample-specific diamagnetic and paramagnetic passive shimming" by Kevin M. Koch et al., (Journal of Magnetic Resonance, Volume 182, pages 66-74, 2006). This article describes the compensation of inhomogeneities of a magnetic field by a passive shimming system for which two materials of opposing magnetic susceptibility are distributed for compensation of inhomogeneities of the appertaining target. The cited article describes implementing a homogenization of a mouse brain at 9.4 T using a prototype of the shim.

The use of shims in light of a transducer embodiment that is important for an accompanying magnetic resonance monitoring of the temperature is, however, not known, and accordingly it is also not known to design medical HIFU devices in such a manner.

According to the invention, at least one shim element (possibly a number of shim elements) is associated with a transducer so that temperature monitoring by magnetic resonance tomography can be improved with regard to possible occurring errors. This in particular pertains not only to errors that are caused by the air filling of the transducer, but also to errors that are caused overall by the transducer design. While water has a susceptibility $-8.0 \times 10^{-6}$ (thus is diamagnetic), air is paramagnetic. The susceptibility of air lies at $0.3 \times 10^{-6}$.

Because the transducer is provided with a suitable shim, or a shim is associated therewith in the transducer environment, differences or deviations and artifacts due to susceptibilities of the transducer in comparison to a surrounding water bath or the like can be at least significantly compensated (counteracted), while accepting deviations that are not to be corrected. Errors in the extremely sensitive temperature monitoring that is based on difference images thus can be avoided.

According to the invention, it is thus prevented in the medical HIFU device that the temperature monitoring that exhibits a sensitivity of 0.01 ppm/K shows apparent temperature disruptions or changes. The importance of such incorrect temperature measurements can be proven experimentally. Disruptions that lie in the range above 15 K are caused by susceptibility changes due to the transducer being filled with air. The correct implementation of HIFU therapy is thereby jeopardized, at least as long as a new reference image is not acquired each time given a re-positioning of the transducer if an elaborate transducer array is not used.

According to the invention, at least one shim element associated with the transducer can be fashioned from graphite and/or bismuth and/or another diamagnetic material having a susceptibility with a magnitude greater than that of the diamagnetism of water, in particular from a strongly diamagnetic material compared with the susceptibility of water.

Shim elements made from different materials can be associated with the transducer in order to compensate the susceptibility changes, or the influencing of the susceptibility by the transducer as optimally as possible. Furthermore, it is possible for individual shim elements to be composed of a number of materials, and specific mixtures can be used or a layer design (for example given plate-shaped elements). Given the use of graphite the correct alignment of the crystal lattice may have to be taken into account. By isostatic pressing the electrical conductivity can be reduced. This is desirable in order to minimize eddy currents due to alternating gradient fields that could disrupt the magnetic resonance imaging. In addition to graphite, bismuth is a further suitable shim material since this material is strongly diamagnetic with a susceptibility of $-164\times10^{-6}$. The susceptibility impairments or influencings due to the transducer or the air in the internal space of a transducer body thus can be at least partially compensated by the selection of suitable shim elements in the correct parameter.

According to the invention, the transducer of the medical device can be fashioned as a monofocal transducer. It is thus a fixed-focus transducer, not a transducer array, so it is a relatively simple embodiment in terms of design. This offers the advantage of a low manufacturing outlay for the HIFU component of the medical device, so the maintenance and the testing of the functionality are likewise simpler relative to the complicated transducer array.

The position of the transducer can be variable (advantageously by means of a mobile mounting arm) relative to a region to be treated with high-intensity focused ultrasound, in particular for treatment of a trajectory (for example a line, a circle, a spiral or a polygon). The mounting arm is advantageously mobile in a number of axes.

By such a position change of the transducer it is possible, for example, to implement a trajectories treatment. The transducer is moved along one trajectory (such as a line or a circle) in order, for example, to be able to treat larger regions of a tumor. In order to alter the position of the transducer or to move it, a mounting arm can be provided that may embody plastic material or synthetic. This mounting arm can be connected with a drive motor that enables movement of the arm at least along one translation direction, and that possibly also allows rotations. It is likewise possible to use a drive that enables a translational movement in the x-direction, y-direction and z-direction in order to be able to optimally reach different treatment regions with the transducer. An adjustment capability in a number of axes is advantageous, for example in two to five axes. The control of the mounting arm can ensue via a control device coupled with a corresponding computer (that possesses a software controller for this) or, respectively, comprising such a corresponding computer. The control device can possibly be identical with the computer.

By the inventive shimming, that shields the transducer with regard to susceptibility changes or differences caused by the transducer or its embodiment, the transducer can be moved without problems below the region to be treated or (given other arrangements) next to or above this region without the temperature monitoring by the magnetic resonance exposures being jeopardized.

According to the invention the device can include a water bath in which the transducer is arranged (in particular such that it can be moved) for coupling of the ultrasound.

The ultrasound coupling normally occurs with water or certain gels. In connection with a therapy with high-intensity focused ultrasound it is advantageous for the transducer to be moved through or in a water bath below the patient. For this purpose, a suitable reservoir is appropriately provided, possibly integrated into a patient bed. For example, the transducer itself can be mounted on an arm-like device, for example on a plastic arm. Such a mounting can be controllable to adjust the position of the transducer via servomotors relative to a region to be treated or to be irradiated in order to thus alter the transducer position in one plane and possibly also in terms of its height.

The magnetic resonance apparatus can be fashioned such that the temperature monitoring ensues using a single reference image retained given a possible position change of the transducer. The temperature monitoring is thus implemented using a reference image for a number of temperature images under possible position change of the transducer. This has the advantage that a new reference does not have to be acquired each time for each change of the position (thus not multiple times in the course of an ultrasound examination or treatment) in order to ensure that the temperature monitoring delivers correct values. Apparent temperature changes and disruptions of the temperature monitoring arising therefrom can be minimized via the shimming, which compensates the susceptibility changes due to the structure or, respectively, the design of the transducer, such that given a monofocal transducer a single reference image is sufficient without noticeable temperature differences occurring even given a distinct change of the position of transducer. For this purpose, the magnetic resonance apparatus has a corresponding control and measurement data processing device that enables the monitoring with a reference.

According to the invention the transducer can be fashioned with at least one shim element, and/or at least one shim element can be provided in proximity to the transducer. In principle two different possibilities for the arrangement of the shim elements thus exist. The first possibility is that the transducer directly includes a shim element that is arranged or attached thereon or therein. Naturally, multiple shim elements can likewise be attached on or in the transducer.

Additionally or alternatively, one or more shim elements can be provided in proximity to the transducer, for example in a specific environment region, and possible position changes of the transducer can be taken into account by a distribution of a number of shim elements or by a mobile arrangement of the shim elements themselves.

The transducer can be fashioned with a shim element and/or a number of shim elements within a transducer housing and/or outside (also below) a transducer housing. The shim elements can thus be arranged on the inside of a housing (for example made from plastic) associated with the transducer or, respectively, be attached outside of this housing. In the case of attachment or arrangement outside of the housing, attachment on the underside (which normally exhibits a larger surface than the possibly angled side regions) is normally appropriate.

Furthermore, at least one plate-shaped and/or disc-shaped shim element can be inventively associated with the transducer. Thus a single shim element can be composed of a number of plates or discs that are stacked atop one another or that are connected with one another in an appropriate manner (for example cemented) in order to form a contiguous shim element. Naturally, a number of plates next to one another (possibly with intervals in-between) can likewise be provided. The plates or discs can in turn be provided directly at the transducer (in particular at a housing) or in its surrounding area.

Given the use of graphite plates, the orientation must be selected to ensure the desired magnetic properties and advantageously to reduce the electrical conductivity, or an isostatic pressing is done to avoid a preferred magnetic direction of the susceptibility, so that the paramagnetic effect of air can be compensated by the strong diamagnetic effect of the graphite.

Alternatively, if a substantially shape-oriented material is used, it should be noted that the axis with the strong diamagnetism lies parallel to the direction of the magnetic field.

Furthermore, the invention concerns an ultrasound transducer (in particular for a medical device as described above) that is fashioned with at least one shim element to compensate susceptibility differences or changes (due to the design of the transducer) for the generation of magnetic resonance exposures. The transducer according to the invention has a shim element attached or arranged on it, or a number of shim elements that, due to their magnetic properties, cancel disruptions of the magnetic field (for example due to air within the transducer) that are disadvantageous for the generation of magnetic resonance exposures. For this purpose, the shim element can be permanently or respectively fixed with the transducer housing by adhesion or bolting or in another manner.

According to the invention the transducer can be fashioned with at least one shim element arranged on the base of a transducer housing and/or at least one shim element arranged on a lateral boundary of a transducer housing, in particular with a shim element arranged on the inside of the housing and/or a shim element arranged on the outside of the housing. Various shim elements (for example plates) can be provided (either internally or externally) in a lower region of the transducer housing can be formed plastic, for example. Furthermore, further shim elements can alternatively or additionally be provided on side walls of the transducer housing. These shim elements can in turn be provided internally and externally on the inside of the housing or on the outside of the housing. The upper transducer region of the transducer normally comprises a piezo-ceramic. Generally it can be advantageous when the shim elements on the outside of the housing are easily removable in order to be able to adapt the shim to the respective conditions in the magnetic field generation, by the shim element being removed or further shim elements being attached. Shim elements on the inside of the housing can be fashioned fixed or likewise removable on the base or in the side region.

The transducer can be fashioned with at least one shim element made from graphite and/or bismuth and/or another diamagnetic material. The transducer can be fashioned with at least one shim element made from a strongly diamagnetic material. The susceptibility of the material is selected such that disruptions of the magnetic field (resulting due to the design of the transducer (in particular due to air filling the transducer)) for the attendant temperature monitoring during the ultrasound therapy are compensated as optimally as possible. The transducer can advantageously be fashioned with at least one plate-shaped and/or at least one disc-shaped shim element.

By the selection of thin plates (of which a number can possibly be used or arranged atop one another), the possibility results to optimize the shim depending on the application.

Moreover, the invention concerns a method for generation of magnetic resonance exposures with temperature monitoring of a region treated or to be treated with high-intensity focused ultrasound, in particular by means of a medical device or using a transducer as described above, in which at least one shim element for compensation of a susceptibility change or difference (caused by the design of the transducer) with regard to the transducer environment is associated with a transducer for generation of the high-intensity focused ultrasound. The inventive method thus substantially compensates apparent temperature changes or temperature disruptions insofar as is possible with a shim that is normally not altered during the therapy, but can also be adapted as needed in the course of treatment. The method compensates susceptibility changes that are caused due to the transducer differing from its environment with regard to material.

The method enables reliable temperature monitoring of HIFU therapy in which a monofocal transducer is used for the ultrasound generation, and additionally only a single reference image must be generated, normally at the beginning of the therapy or directly preceding the therapy.

The subject matter of the method is basically the temperature monitoring, thus a measurement process. This occurs contemporaneously with a treatment with high-intensity ultrasound, the details of the treatment itself not being the subject matter of the inventive method. The temperature monitoring with the magnetic resonance system (thus, for example, a magnetic resonance apparatus as described above) can ensue wholly automatically using a computer programmed with measurement software, or can be implemented with monitoring by a suitably qualified person, for example a technician or physician. Furthermore, it is possible for the person responsible for the generation of the magnetic resonance exposures with the temperature measurement to select or input parameters for the data acquisition during the measurement or preceding the measurement while the temperature monitoring otherwise runs automatically.

If a transducer is used at which a shim element is located, or that has shim elements arranged in the environment thereof, susceptibility changes or deviations and artifacts that can negatively influence the temperature measurement can be substantially canceled (counteracted). Temperature disruptions in the very sensitive phase images of the magnetic resonance measurement are thereby avoided. The paramagnetic effect (that is caused, for example, by air filling the transducer) thus can be compensated. The induced susceptibility artifacts can be minimized by using graphite elements and the like. The monofocal HIFU transducer can be moved without it being necessary to acquire new reference images. More elaborate measurements or treatments such as a trajectories treatment are made possible without difficulty. At the same time elaborate transducer arrays can thereby be foregone.

BRIEF DESCRIPTION OF THE DRAWINGS

FIG. 4 is a flowchart for generation of magnetic resonance exposures in an embodiment of the inventive method.

DESCRIPTION OF THE PREFERRED EMBODIMENTS

Figure 1:
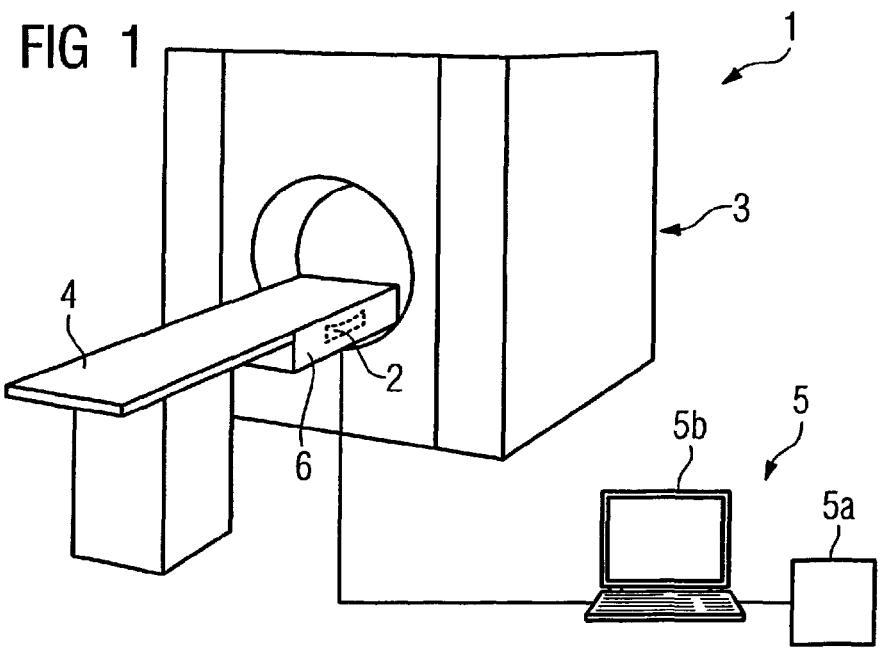
FIG. 1 schematically illustrates an inventive medical device.

An inventive medical device 1 is shown in FIG. 1. In addition to a transducer 2 (that here is only indicated in outline), the medical device 1 has a magnetic resonance apparatus 3 with which magnetic resonance exposures can be generated. The purpose of the generation of the magnetic resonance exposures with the medical device 1, namely with the magnetic resonance apparatus 3 thereof is temperature monitoring of therapy with high-intensity focused ultrasound (HIFU therapy). Such implemented therapy is, for example, in order to destroy tumors by heating the tumor tissue.

For this purpose, a patient (not shown) is supported on a bed 4, the patient being treated with ultrasound that is generated by the transducer 2 while magnetic resonance exposures are generated with the magnetic resonance apparatus 3 concomitantly, or possibly shortly before or after the ultrasound treatment. The magnetic resonance exposures (images) can be used for depiction of the region to be treated, but in any case serve for temperature monitoring of the ultrasound treatment. The temperature monitoring ensures that the generated heating is high enough in order to destroy the tumor tissue, but is not so high in the surroundings such that healthy tissue is damaged.

The medical device 1 furthermore has a control device 5, here a computer 5a with an associated image output and entry input console 5b. The ultrasound generation for the HIFU therapy is controlled with the control device 5, with the transducer 2 being moved into a surrounding water bath 6 by actuators (not shown) in order to optimally control the treatment region. Furthermore, the generation of the magnetic resonance exposures with the magnetic resonance apparatus 3 is controlled via the control device 5.

In alternative embodiments of a medical device 1, different control devices 5 can possibly be present that embody the computer 5a and image output and entry input console 5b, particularly in the event that further inputs by an operator are required during the treatment so that the physician can monitor or implement the ultrasound treatment while at the same time a technician conducts the temperature measurement with the aid of the magnetic resonance apparatus 3.

For the temperature monitoring with the aid of the magnetic resonance apparatus 3, a reference image is initially generated in order to be able to detect temperature changes using difference images.

The transducer 2 shown here is provided with various shim elements with which susceptibility changes or differences that are due to the design of the transducer 2 (in particular in that the transducer 2 is significantly filled with air) can be compensated. An apparent paramagnetic effect that arises due to the air filling of the transducer in diamagnetic water thus can be at substantially compensated (counteracted).

It is possible that the transducer 2 can be displaced (i.e, its position changed) during the ultrasound treatment with the aid of the control device 5, for example in order to treat larger tumor regions, without new reference images having to be acquired each time for the accompanying temperature monitoring with the aid of the magnetic resonance apparatus 3. With the medical device 1, the temperature monitoring can ensue with a single reference image. The transducer 2 is a monofocal transducer and thus is designed more simply in terms of construction than the elaborate transducer arrays.

Figure 2:
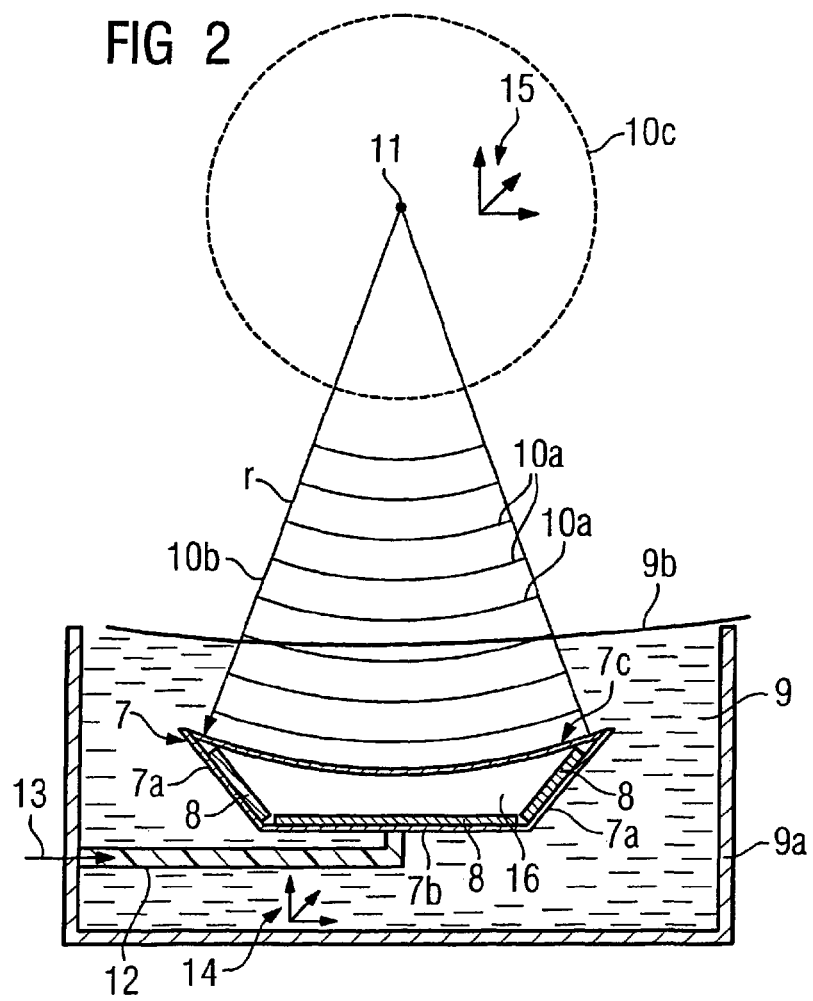
FIG. 2 shows an arrangement of a transducer with shim elements in an inventive medical device.

An arrangement of a transducer 7 with shim elements 8 in an inventive medical device is shown in FIG. 2. The transducer 7 is located in a water bath 9 that ensures the coupling of the ultrasound (that is generated with the aid of the transducer 7) with a region of the patient to be treated with ultrasound, this region being defined by the skin 9b. Furthermore, the transducer 7 has a housing with lateral boundaries 7a and a base 7b as well as an upper shell region 7c, which is the actual transducer region made from a piezo-ceramic.

The ultrasound generation made by the transducer 7 is indicated by the sound waves 10a or the sound cone 10b. The ultrasound generation by the transducer 7 is monofocal; there is thus a single focal point 11. The circle around the focal point 11, at which the upper sound region 7c forms a portion of the circle line, has a radius r. The position of the transducer 7 itself is altered to vary this focal point 11. In the shown arrangement this occurs by a mounting arm 12 that, for example, is formed of a plastic material. The mounting arm 12 is controlled by servomotors (not shown here), indicated by the arrow 13. It is thereby possible (as indicated by the arrows 14) to move the transducer 7 in the x-direction, y-direction and z-direction, thus in a horizontal plane as well as vertical thereto. The position of the focal point 11 (indicated by the arrows 15) changes correspondingly. For example, larger regions of a tumor can thus be treated. In different embodiments rotation of the mounting arm 12 can also be possible.

The transducer 7 itself is formed of materials that are nearly non-magnetic in comparison to the surrounding diamagnetic water. For example, air 17 is located in the transducer 7. This "missing diamagnetism" (which, among other things, would interfere with temperature monitoring with a magnetic resonance apparatus to the extent that for a significantly reliable temperature monitoring a new reference image would have to be generated given each change of the position of the transducer 7 due to movement of the mounting arm 12) is significantly compensated by the shim elements 8 (here fashioned plate-shaped) in the inner region of the transducer 7.

According to the invention disruptive effects that can cause an apparent temperature change in the range of more than 15 K can be minimized by, as shown here, attaching shim elements 8 inside the transducer 7 on the lateral boundaries 7a and floor 7b, for example.

A treatment region 10c is presently irradiated with the ultrasound that is generated with the transducer 7, and the position of the transducer 7 must be correspondingly changed within the treatment region 10c for an irradiation of a larger region. For this purpose, the transducer 7 is moved in the water bath 9 with the boundaries 9a.

Examples of different embodiments of inventive transducers are shown in FIGS. 3A through 3D, without intending to be exhaustive.

Figure 3A:
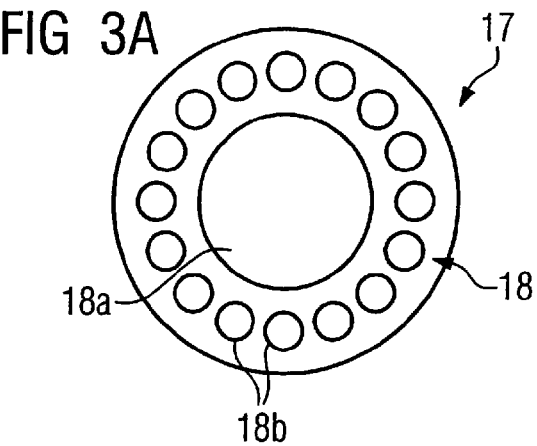
FIGS. 3A-3D respectively show embodiments of inventive transducers.

In FIG. 3A a transducer 17 is shown from below. The transducer 17 has various shim elements 18 that are distributed as thin plates on a housing 17. The shim elements 18 include a central disc as a shim element 18a that is arranged centrally in a central region of the transducer 17. Further shim elements 18b surround this central shim element 18a as likewise round plates, but that are fashioned smaller than the shim element 18a. The shim elements 18b are arranged in a higher-situated upper region in a transducer housing as in FIG. 3C, which transducer housing has a base region with a step.

In an alternative embodiment (not shown), the further shim elements 18b are not used. The shim is then formed only by the shim element 18a.

The shim elements 18 of the transducer 17 (the further housing components and the mounting in a water bath not being shown) enable the compensation of susceptibility changes or differences that are caused by the design of the transducer 17 itself. For this the shim elements 18 are formed of diamagnetic graphite that, for example, is isostatically pressed to avoid a preferential orientation of the crystal seeds in the material and exhibits a plate thickness in the millimeter range.

Figure 3B:
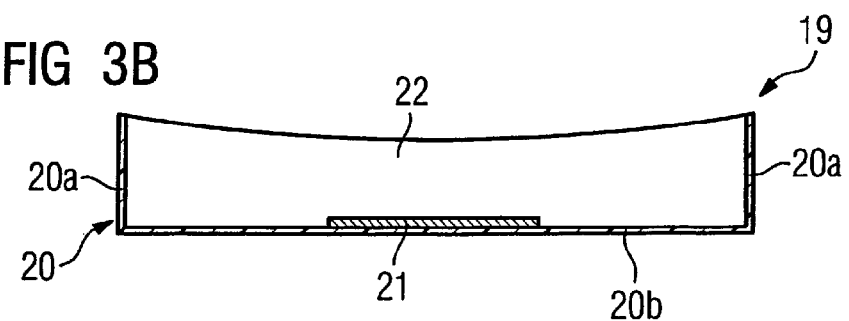

A further transducer 19 is shown in FIG. 3B. This transducer 19 has a housing 20 made of plastic with lateral boundaries 20a as well as a base 20b. A shim element 21 (which is a bismuth disc) is arranged inside the housing 20 on the floor 20b, which shim element 21, due to its diamagnetic properties, can cancel out the paramagnetic effects that are caused by the air 22 that is located in the transducer housing 20.

Figure 3C:
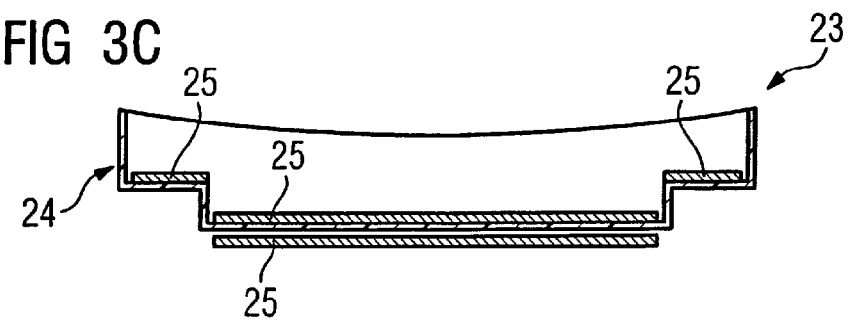

A number of shim elements 25 are provided in the transducer 23 of FIG. 3C (which likewise has a housing 24 made from plastic and a piezo-ceramic transducer region), which shim elements 25 are arranged on the outside and inside of the housing 24. The shim elements 25 are partially composed of layers; a number of shim plates thus are used depending on which shim is optimal for the respective temperature monitoring in the ultrasound therapy. For adaptation the shim elements 25 can be removed, in particular in the outer region of the housing 24. This is enabled via a positive mounting (not shown). Given vertical side boundaries the housing 24 exhibits a stepped floor region, whereby here shim elements 25 are located on every level.

Figure 3D:
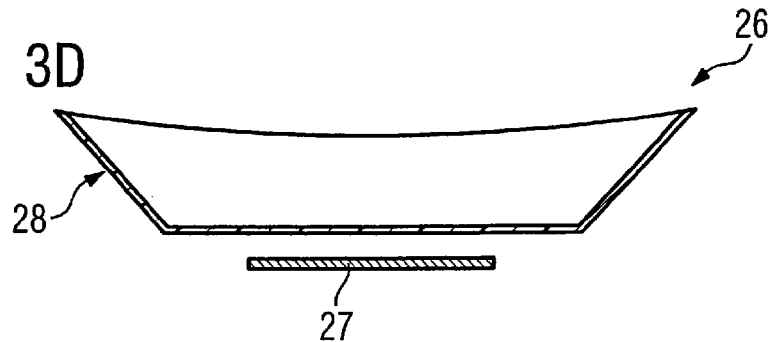

In the transducer 26 of FIG. 3D a shim element 27 is located in the near surroundings of the transducer housing 28 without being directly attached on this. If necessary it is therewith possible to move the transducer 26 and the shim element 27 independent of one another in order to optimize the adjustment of the shim. Nevertheless, the shim element 27 exhibits such a spatial proximity to the transducer 26 that the disruptions of the magnetic field or, respectively, the disruptions of the homogeneity of the magnetic field that are caused by the transducer 26 can be suitably canceled out by the shim element 27. The mounting for the shim element 27 is not shown.

A flowchart for generation of magnetic resonance exposures in an inventive method is presented in FIG. 4. According to step a the transducer is accordingly suitably positioned for the generation of the high-intensity focused ultrasound; the shim element or shim elements are similarly positioned with the transducer in the surroundings of the transducer.

A reference image for the temperature monitoring with a transducer located at a first position is subsequently acquired in step b. Ultrasound radiation is subsequently radiated and a first magnetic resonance phase image is acquired in order to enable a temperature determination of the region to be treated using the subtracted image exposures.

The ultrasound treatment is continued according to step c, wherein the temperature monitoring is likewise further implemented. A re-positioning of the transducer, which for this can be moved into a surrounding water bath with the aid of suitable servomotors or also manually, ensues in the framework of the treatment.

According to step d a magnetic resonance phase image is again acquired subsequent to or simultaneously with the temperature monitoring, which magnetic resonance phase image allows a temperature image calculation based on the reference image that was generated in step b.

In spite of the repositioning of the transducer, no new reference image must be acquired since, in addition to the transducer, the shim element was also re-positioned or a shim is furthermore present in the environment of the transducer, such that susceptibility artifacts are minimized.

According to the invention a compensation of susceptibilities using materials of very different susceptibilities (in particular paramagnetic and strongly diamagnetic materials) is inventively implemented given an accompanying temperature measurement during an ultrasound treatment. Such a shim method that is based on different susceptibilities is thus advantageously used for the temperature monitoring in connection with transducers that serve for ultrasound generation. As the generation of a new reference image given each change of the position of the monofocal transducer, elaborate transducer arrays can be foregone.

If the transducer is newly repositioned (thus step c is executed again), according to the step d an MR phase image is generated again without a new reference image being acquired. Due to the shim this temperature image shows no noteworthy disruptions of the temperature.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical device comprising:
   a transducer configured to generate high intensity focused ultrasound for a treatment of a subject by elevating a temperature of tissue in the subject, said transducer being comprised of material that produces a susceptibility difference between said transducer and an environment of said transducer;
   a magnetic resonance apparatus configured to generate magnetic resonance exposures that represent the temperature of said tissue during said treatment, said magnetic resonance apparatus being configured to generate a magnetic field that participates in generation of said magnetic resonance exposures, and said susceptibility difference causing a disruption of said magnetic field that produces an error in the temperature representation in magnetic resonance exposures; and
   a shim element having a material composition that gives the shim element a shimming effect, with said shim effect being located at a location relative to said transducer that causes said shimming effect of said shim element to counteract said susceptibility difference and reduce said disruption of said magnetic field and said error in said temperature representation in said magnetic resonance exposures.

2. A medical device as claimed in claim 1 wherein said shim element is comprised of a diamagnetic material having a susceptibility with a magnitude that is greater than the susceptibility of water.

3. A medical device as claimed in claim 1 wherein said transducer is comprised of material selected from the group consisting of graphite and bismuth.

4. A medical device as claimed in claim 1 comprising a mobile mounting arm to which said transducer is mounted that is operable to change a position of the transducer relative to said tissue.

5. A medical device as claimed in claim 1 comprising a water bath in which said transducer is contained during said treatment to couple said high intensity focused ultrasound with said subject.

6. A medical device as claimed in claim 4 wherein said magnetic resonance apparatus generates a reference image for each of a plurality of temperature ranges respectively for different positions of said transducer.

7. A medical device as claimed in claim 1 wherein said shim element is mechanically combined with said transducer.

8. A medical device as claimed in claim 1 wherein said shim element is disposed separately from said transducer but sufficiently proximate said transducer to compensate said susceptibility difference.

9. A medical device as claimed in claim 1 wherein said transducer comprises a transducer housing, and wherein said shim element is associated with said transducer at a location selected from the group consisting of inside said transducer housing and outside said transducer housing.

10. A medical device as claimed in claim 1 wherein said shim element has a configuration selected from the group consisting of a plate configuration and a disk configuration.

11. An ultrasound transducer comprising:
- a transducer arrangement that generates and emits ultrasound into an environment of the transducer arrangement, said transducer arrangement being comprised of material having a susceptibility difference relative to said environment; and
- a shim element having a material composition that gives the shim element a shimming effect, and being mechanically attached to said transducer arrangement at a location relative to said transducer arrangement that causes said shimming effect of said shim element to counteract said susceptibility difference.

12. An ultrasound transducer as claimed in claim 11 wherein said transducer arrangement comprises a transducer housing having a base and a lateral boundary, and wherein said shim element is located at a position selected from the group consisting of on said base, on said lateral boundary, inside said transducer housing, and outside said transducer housing.

13. An ultrasound transducer as claimed in claim 11 wherein said shim element is comprised of a diamagnetic material having a susceptibility with a magnitude that is greater than the susceptibility of water.

14. An ultrasound transducer as claimed in claim 11 wherein said transducer is comprised of material selected from the group consisting of graphite and bismuth.

15. An ultrasound transducer as claimed in claim 11 wherein said shim element has a configuration selected from the group consisting of a plate configuration and a disk configuration.

16. A method for monitoring temperature in tissue being treated with high intensity focused ultrasound using a transducer that generates high intensity focused ultrasound for a treatment of a subject by elevating a temperature of tissue in the subject, said transducer being comprised of material that produces a susceptibility difference between said transducer and an environment of said transducer, comprising the steps of:

with a magnetic resonance apparatus, generating magnetic resonance exposures that represent the temperature of said tissue during said treatment, said magnetic resonance apparatus being configured to generate a magnetic field that participates in generation of said magnetic resonance exposures, and said susceptibility difference causing a disruption of said magnetic field that produces an error in the temperature representation in magnetic resonance exposures; and reducing said disruptions in said magnetic resonance exposures by providing a shim element with a material composition that gives the shim element a shimming effect, and placing said shim element at a location relative to said transducer that causes said shimming effect of said shim element to counteract said susceptibility difference and reduce said disruption of said magnetic field and said error in said temperature representation in said magnetic resonance exposures.

* * * * *